United States Patent [19]

Roberts et al.

[11] 3,959,214

[45] May 25, 1976

[54] CYCLIC AMINE STABILIZERS

[75] Inventors: James Stewart Roberts; Robert Lyle Craig, both of Stirling, Scotland

[73] Assignee: Imperial Chemical Industries Limited, London, England

[22] Filed: Sept. 13, 1973

[21] Appl. No.: 396,664

[30] Foreign Application Priority Data

Sept. 13, 1972 United Kingdom............. 42444/72

[52] U.S. Cl.................. 260/45.8 N; 260/45.8 NZ; 260/45.8 R; 260/45.8 SN
[51] Int. Cl.²................... C08K 5/34; C08K 5/35; C08K 5/46; C08L 23/02
[58] Field of Search ............... 260/45.8 N, 45.8 NZ

[56] References Cited
UNITED STATES PATENTS

| | | | |
|---|---|---|---|
| 3,334,103 | 8/1967 | Feldman et al. | 260/290 |
| 3,436,369 | 4/1969 | Kitaoka et al. | 260/45.8 |
| 3,474,068 | 10/1969 | Murayama et al. | 260/45.8 |
| 3,705,126 | 12/1972 | Matsui et al. | 260/45.8 |

*Primary Examiner*—Donald E. Czaja
*Assistant Examiner*—R. A. White
*Attorney, Agent, or Firm*—Cushman, Darby & Cushman

[57] ABSTRACT

Cyclic amines of formula

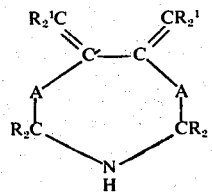

where
R = hydrocarbyl or substituted hydrocarbyl
R¹ = hydrogen, hydrocarbyl or substituted hydrocarbyl and
A = a divalent group or a direct link
are prepared from the corresponding dialkyl cycloalkenylamines. The cyclic amines may be converted to cyclic nitroxide radicals by oxidation and to bicyclic amines by Diels-Alder addition, and are useful as UV stabilisers for polyolefins.

10 Claims, No Drawings

CYCLIC AMINE STABILIZERS

This invention relates to cyclic amines and nitroxide radicals, and to processes for preparing them.

According to one aspect of the present invention, we provide cyclic amines of formula:

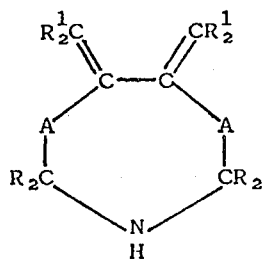

I where each group R, which may be the same or different is a hydrocarbon or substituted hydrocarbon group; each group $R^1$, which may be the same or different, is hydrogen or a hydrocarbon or substituted hydrocarbon group; and each group A, which may be the same or different, is a divalent group or a direct link.

The groups R may each be aliphatic, alicyclic or aromatic (for example, aryl, aralkyl or alkaryl), and may be substituted or unsubstituted. In addition, the two R groups attached to the same ring carbon atom may themselves be linked together so as to form a second ring which, with the nitrogen-containing ring, forms a spiro ring system. Steric factors may prevent the inclusion of large or bulky groups or substituents, but apart from such factors, there does not appear to be any upper limit to the size of the groups R. Straight and branched chain alkyl groups, for example having 1-10 carbon atoms, are convenient and are therefore preferred. Where two R groups on the same ring carbon atom are linked to form a second ring, the combined two R groups are preferably of the structure $-CH_2)_n$, where n is an integer between 3 and 9.

The groups R may also include hetero atoms, for example, oxygen, sulphur, nitrogen or phosphorus within a carbon chain, and may also include olefinic double bonds in a carbon chain or in an alicyclic ring.

The groups $R^1$ may be of the same types as the groups R listed above, but preferably $R^1$ is hydrogen; that is, the compounds according to the invention preferably contain two vicinal exocyclic methylene groups.

The groups A may for example be $-CH_2)_n$ where n is an integer, or $-O-$, but preferably both of the groups A are direct links, that is, the compounds according to the invention preferably contain the 5-membered pyrrolidine ring system.

Preferred compounds according to the invention accordingly have the formula

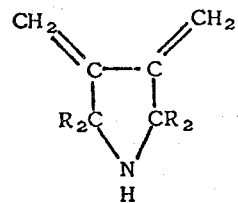

II where R is a straight or branched chain alkyl group having 1–10 carbon atoms, for example methyl, ethyl and isopropyl, or the two R groups on the same ring carbon atom are linked to form a spiro-fused 4-10 membered aliphatic ring.

Cyclic amines according to the invention may be useful as antioxidants and stabilizers, particularly as stabilizers for the protection of polyolefin materials against degradation by ultraviolet light when used in quantities in the range 0.01–1%, preferably 0.1–1% by weight of the polyolefin material. Because of their vicinal exocyclic double bonds they may enter into Diels-Alder reactions with conventional dienophiles and thereby produce other cyclic amines which may be useful as antioxidants and stabilizers.

Thus, compounds of formulae III, IV and V may be produced by the reaction of cyclic amines of formula I with dienophiles containing olefinic, acetylenic and azo bonds respectively.

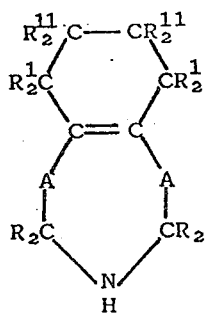 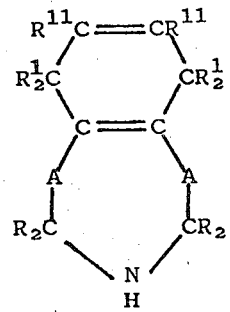 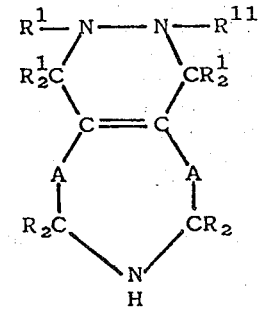

III  IV  V

In the above formulae, the groups $R^{11}$, which may be the same or different, are hydrogen or hydrocarbon or substituted hydrocarbon groups provided that at least one of the groups $R^{11}$ must be an electron withdrawing group for example $-COOH$, $-COOR_1$ and $-COR_1$ where $R_1$ is alkyl or aryl, $-CHO$ and $-CN$. Two of the $R^{11}$ groups may be joined together to give a difunctional electron withdrawing group for example $-CO-O-CO-$ (anhydrides) and $-CO-CH=CH-CO-$ (quinones), or may be joined together to form an alicyclic ring system for example a cyclopentene or cyclohexene.

Suitable dienophiles include for example maleic anhydride, dimethyl acetylene-dicarboxylate and diethyl azodicarboxylate. The products of the addition of these dienophiles to 3,4-dimethylene-2,2,5,5-tetramethylpyrrolidine are shown in formulae VI–VIII respectively, where Me = methyl and Et = ethyl.

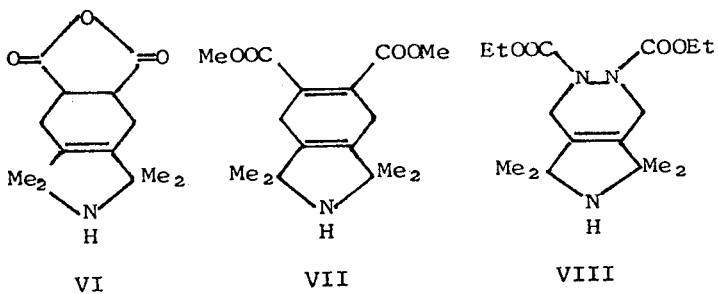

VI          VII          VIII

These compounds may also be prepared by reaction of a dienophile with the 'protected' amine formed at stage (c) of the process described below for the preparation of cyclic amines according to the invention, followed by removal of the protecting group.

In addition, cyclic amines according to the invention may be oxidised, for example by hydrogen peroxide or an organic per-acid, to the corresponding nitroxide radicals of formula:

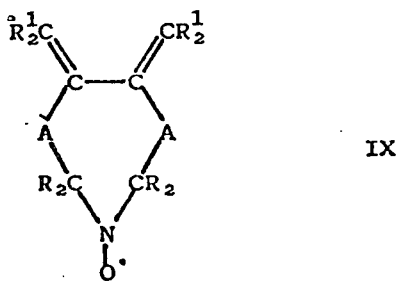

IX where R, $R^1$ and A are as previously defined.

These compounds are generally more or less stable crystalline solids, having a yellow/orange colour and a camphoraceous smell. Their electron spin resonance (e.s.r.) spectrum exhibits a 1:1:1 triplet characteristic of a radical species containing a nitrogen atom, with a hyperfine splitting $a_N$, usually in the range 14–17 G, and a magnetogyric ratio, $g$, around 2.

As stable radical species, these compounds can have useful properties. For example, certain compounds may be used as anti-oxidants, particularly for polymeric materials, for example natural or synthetic rubbers. Alternatively, because of their e.s.r. characteristics, the compounds may be incorporated into a reaction system and used as spin labels.

Cyclic amines of formula I may be prepared as described below from the dialkyl cycloalkenyl amines of structure X

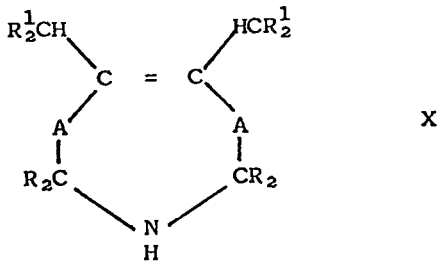

X where R, $R^1$ and A are as defined above, provided that A does not include allylic hydrogen atoms $\alpha$ to the olefinic double bond.

Such amines may be prepared in known manner, for example by reductive cyclisation of a dipropargyl amine.

According to another aspect of the present invention, we provide a process for the preparation of a cyclic amine of formula I from a substituted cycloalkenylamine of formula X above, comprising the steps of a. Protection of the amino nitrogen atom by conversion to a derivative which is inert under the subsequent reaction conditions, b. Substitution of halogen for both allylic hydrogen atoms shown in formula X $\alpha$ to the olefinic double bond, c. Dehalogenation of the resultant dihalosubstituted cycloalkenyl-amine derivative, and d. Reconversion of the amine-derivative to an di-alkYlidene-substituted cyclic amine.

It will be appreciated that 'alkylidene' is intended to include the methylene group, that is, where each $R^1$ is hydrogen, but that, in any event, only one hydrogen atom on each alpha carbon atom is replaced by halogen.

The amino nitrogen atom may be protected in a number of ways, by forming a derivative that is inert under the subsequent reaction conditions, but can readily be re-converted to an amine. For example, it may be reacted with an isocyanate to form a urea. Conveniently, the amine is reacted with a carboxylic acid halide or anhydride to form the corresponding amide. The amine can then be regenerated in conventional manner by hydrolysis.

The halogenating agent must be such that both allylic hydrogen atoms are replaced by halogen, so that the amine derivative includes the structure

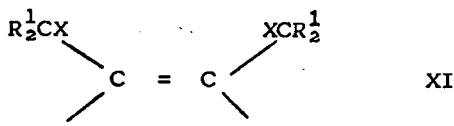

XI where $R^1$ is as hereinbefore defined and X is halogen. A particularly convenient halogenating agent, because of its propensity to enter into allylic substitution reactions, is N-bromosuccinimide, but other halogen sources, for example N-chlorosuccinimide, may be used if required. It is preferred that the halogen is chlorine, bromine or iodine, particularly bromine and iodine.

The dihalo-substituted compound may be dehalogenated, and thus be converted to a di-alkylidene-substituted compound in any convenient manner, for example by reaction with a sufficiently electropositive metal, that is, a metal having sufficient affinity for halogen to break the carbon-halogen bond. Zinc dust has been found to be a convenient reagent.

On completion of the reaction the amine is then regenerated as appropriate, and as described above, the cyclic amine may then be oxidised to the cyclic nitroxide radical, for example by oxidation with a peroxide.

The above reaction sequence is particularly applicable to amines of structure X above where each A is a direct link, that is where the starting material is a 3,4-dialkyl-3-pyrolline derivative, of structure

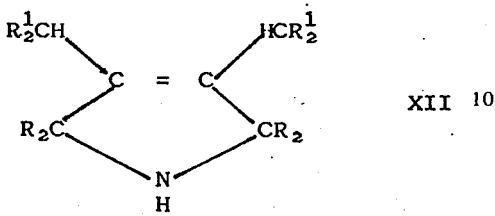

XII where R is a hydrocarbon or substituted hydrocarbon group and $R^1$ is hydrogen or a hydrocarbon or substituted hydrocarbon group, but is preferably hydrogen.

Using the 3,4-dialkyl-3-pyrolline derivatives as an example, the whole reaction sequence, including production of the nitroxide radical, may be represented as follows:

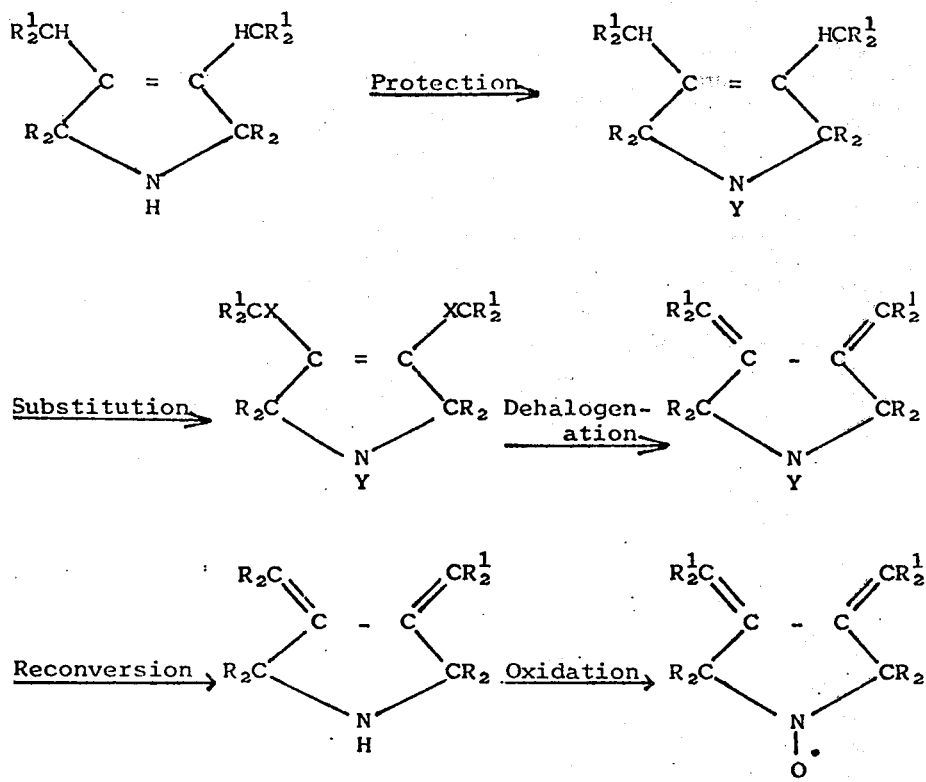

where R and $R^1$ are as defined above, X is halogen, for example bromine, and Y is an organic group, for example acyl.

The invention is now illustrated by the following Examples, in which parts by weight and parts by volume bear the same relation as do kg and $dm^3$. Yields are mole % of the theoretical yields, calculated on the basis of unpurified product.

EXAMPLE 1

3,4-Dimethylene-2,2,5,5-tetramethylpyrrolidine 2,2,3,4,5,5-Hexamethyl-3-pyrroline

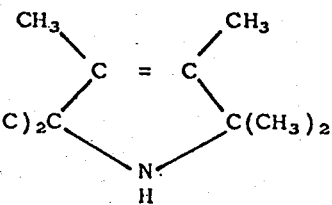

was prepared by reduction, using sodium in liquid ammonia, of bis(1,1-dimethylpropargyl)amine, according to the method of G F Hennion and C V DiGiovanna, J. Org. Chem. 30, 2645, (1965).

a. Protection of the amine starting material

A solution of 2,2,3,4,5,5-hexamethyl-3-pyrroline (15 parts by weight) in dry pyridine (18 parts by weight) and dry methylene chloride (300 parts by volume) was cooled to 0°C in an ice bath. To this cooled solution, a solution of trifluoroacetic anhydride (69 parts by volume) in dry methylene chloride (150 parts by volume) was added dropwise, with stirring, over a period of 1¼ hours. The solution was stirred for a further 3 hours, during which time it was allowed to reach room temperature, and was subsequently left standing overnight. To this solution crushed ice (150 parts by weight) was added with stirring, followed by methylene chloride (200 parts by volume) and water (100 parts by volume). After separation from the aqueous phase, the organic extract was washed with 1M hydrochloric acid solution (100 parts by volume) followed by saturated brine solution (100 parts by volume), and was subsequently dried over anhydrous potassium carbonate. The solvent was removed under reduced pressure to yield a dark-coloured oil (24.4 parts by weight; 100% yield). This material was used without further purification in the next stage.

Purification could be effected either by preparative thin-layer chromatography (20% ether/60–80 petroleum ether) or by column chromatography on Grade III neutral alumina eluting with 10% ether/40-60 petroleum ether. The product, 1-trifluoroacetyl-2,2,3,4,5,5-hexamethyl-3-pyrroline, was identified by its melting point and infrared and nuclear magnetic resonance spectra. (Melting point: ~ 20°C).

$\nu_{max}$ (CCl$_4$) = 1665, 1210, 1165, 1145 and 1050 cm$^{-1}$;

$\tau$ CDCl$_3$) = 8.48 (s, 12H) and 8.37 (s, 6H).

b. Substitution with Halogen

To a solution of the crude amide product of stage (a) (15 parts by weight) in dry carbon tetrachloride (700 parts by volume) was added crude amorphous N-bromo succinimide (30.6 parts by weight) and dibenzoyl peroxide (0.72 parts by weight). The resultant heterogeneous solution was refluxed for 40 minutes. The less dense succinimide was removed by filtration and the solvent was removed under reduced pressure to yield a semicrystalline brown oil (27.4 parts by weight; 112% yield). This material was used without further purification in the next stage.

Purification could be effected either by column chromatography on Grade III neutral alumina eluting with 10% ether/40–60 petroleum ether or by preparative thinlayer chromatography (20% ether/60–80 petroleum ether).

The product, 1-trifluoroacetyl-3,4-di(bromomethyl)-2,2,5,5-tetramethyl-3-pyrroline, was identified by its melting point and infra-red and nuclear magnetic resonance spectra. (Melting point: 42°–44°C).

$\nu_{max}$(CCl$_4$) = 1670, 1375, 1210, 1160, 1145, 1050, 890, 650 and 580 cm$^{-1}$;

$\tau$ (CDCl$_3$) = 8.35 (s, 12H) and 5.95 (s, 4H).

c. Debromination

Zinc dust was activated by sequential washing with 5% hydrochloric acid, water, methanol, and ether, and was then dried. 18 Parts by weight of this zinc dust was added to a solution of the crude dibromide of stage (b) (27.4 parts by weight) in dry dimethylformamide (500 parts by volume). The resultant heterogeneous solution was stirred vigorously at 105°C for 2 hours (reflux condenser fitted). After cooling, water (400 parts by volume) and ether (400 parts by volume) were added, the insoluble inorganic material was removed by filtration, and the filtrate was shaken vigorously in a separating funnel. The aqueous layer was run off and extracted with ether (2 × 200 parts by volume). The ethereal extracts were combined and dried over anhydrous potassium carbonate, and the solvent was removed under reduced pressure to yield a dark-coloured oil. This material was purified by column chromatography (Grade III neutral alumina (150 parts by weight) eluting with 10% ether/40–60 petroleum ether). The product (8.62 parts by weight; 52% yield) was collected in one fraction after removal of the solvent under reduced pressure. This material was used without further purification in the next stage.

Further purification could be achieved by preparative thin-layer chromatography (20% ether/60–80 petroleum ether).

The product was identified as 1-trifluoroacetyl-3,4-dimethylene-2,2,5,5-tetramethylpyrrolidine by its melting point and infra-red, nuclear magnetic resonance and ultra-violet spectra. (Melting point: 39°–41°C).

$\nu_{max}$ (CCl$_4$) = 1670, 1415, 1215, 1150, 1050, 895 cm$^{-1}$;

$\tau$ (CDCl$_3$) = 8.39 (s, 12H), 5.02 (s, 2H), and 4.47 (s, 2H);

$\lambda_{max}$(hexane) = 240 nm ($\epsilon$ = 6040).

d. Regeneration of the amine

A solution of the amide of stage (c) (1.86 parts by weight) in dry, redistilled tetrahydrofuran (50 parts by volume) was cooled to 0°C in an ice bath. To this cooled solution, a solution of potassium t-butoxide (2.1 parts by weight) in dry tetrahydrofuran (100 parts by volume) was added dropwise with stirring over a period of 10 minutes. After stirring at 0°C for a further 20 minutes, the solvent was carefully removed under reduced pressure using a Vigreux column. Water (50 parts by volume) and ether (1000 parts by volume) were added to the resultant solid mass and, after shaking in a separating funnel, the aqueous layer was run off and discarded. The ethereal layer was extracted with 2.5M hydrochloric acid solution (3 × 100 parts by volume) and the acidic extracts were basified by addition of concentrated aqueous potassium hydroxide solution with cooling. The resultant basic solution was saturated with sodium chloride and extracted with ether (3 × 250 parts by volume). The ether extracts were washed with saturated brine solution (100 parts by volume) and dried over anhydrous potassium carbonate. Careful removal of the solvent under reduced pressure using a Vigreux column yielded a slightly yellow-coloured liquid (0.78 part by weight; 69% yield). Distillation under reduced pressure gave a colourless liquid, boiling point 50°–55°C/~ 12 mm Hg pressure.

The material was identified as 3,4-dimethylene-2,2,5,5-tetramethylpyrrolidine by its boiling point and infra-red, nuclear magnetic resonance and ultra-violet spectra.

$\nu_{max}$ (liq. film) = 3040, 1360, 1170, 995 and 885 cm$^{-1}$;

$\tau$ (CDCl$_3$) = 8.69 (s, 12H), 5.13 (s, 2H) and 4.57 (s, 2H);

$\lambda_{max}$ (hexane) = 244 nm ($\epsilon$ = 5960).

Crysalline adducts were obtained in good yield by reaction of the material with maleic anhydride, dimethyl acetylenedicarboxylate and diethyl azodicarboxylate. Typical reaction conditions involved the dissolution of equimolar amounts of the amine and the dieneophile in dry benzene and setting the mixture aside at room temperature for approximately 4 days. Removal of the solvent yielded the crude adduct, which was then purified by recrystallisation.

EXAMPLE 2

Preparation of 3,4-dimethylene-2,2,5,5-tetramethylpyrrolidine-1-oxyl

To a solution of the amine of Example 1 (0.78 parts by weight) in dry methylene chloride (31 parts by volume) was added disodium hydrogen phosphate (1.3 parts by weight). The solution was cooled to 0°C in an ice bath and a solution of m-chloroperbenzoic acid (0.97 parts by weight) in dry methylene chloride (47 parts by volume) was added dropwise with stirring over a period of 30 minutes. After stirring at 0°C for a further 1½ hours, methylene chloride (100 parts by volume) was added, and the solution was washed with 10% aqueous sodium sulphite solution (50 parts by volume) followed by 5% aqueous sodium bicarbonate solution (50 parts by volume). The aqueous washings were discarded, and the organic extract was washed with saturated brine solution (25 parts by volume) and then dried over anhydrous potassium carbonate. Careful removal of the solvent under reduced pressure using a Vigreux column yielded the yellow-orange crystalline 3,4-dimethylene-2,2,5,5-tetramethylpyrrolidine-1-oxyl (0.736 parts by weight; 86% yield).

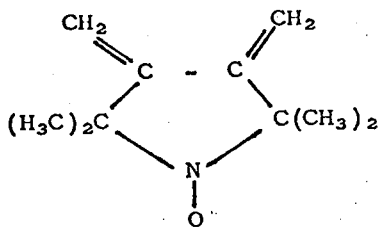

Purification was effected by preparative thin-layer chromatography (30% ether/60–80 petroleum ether).

The overall yield, calculated on the basis of initial hexamethylpyrroline, was about 30%.

The product was characterized by its melting point, infra-red, nuclear magnetic resonance, ultra-violet and electron spin resonance spectra. (Melting point 92°–94°C).

$\nu_{max}$ (Nujol mull) = 1370, 1355, 1185, 1165, 920, 910, 800 and 730 cm$^{-1}$;

$\tau$ (CDCl$_3$ + hydrazobenzene) = 8.70 (s, 12H), 5.08 (s, 2H) and 4.52 (s, 2H).

$\lambda_{max}$ (hexane) = 237 nm ($\epsilon$ = 5200) and 430 nm ($\epsilon$~8).

$a_N$ = 13.7G, g = 2.006.

EXAMPLE 3

Use of 3,4-dimethylene-2,2,5,5-tetramethylpyrrolidine as UV stabiliser

A sample of polypropylene powder containing 0.1% by weight of 1,1,1,1-tetrakis(3',5'-di tert-butyl-4'-/hydroxyphenylpropionyl oxymethyl)methane, a commercial antioxidant, is blended with 0.5% by weight of the product of Example 1, and compression moulded at 220°C into a sheet of thickness 500 μm. A second sheet is moulded containing the above antioxidant, but none of the product of Example 1. Both sheets are simultaneously exposed to test conditions on a Zenotest 150 accelerated weathering apparatus and tested at intervals by flexure. The unmodified sheet becomes embrittled after 500–600 hours, while the sheet containing the product of Example 1 is not embrittled after 2000 hours.

What we claim is:

1. A polyolefin material stabilized against ultraviolet light in admixture with a stabilizing amount of a cyclic amine of the formula:

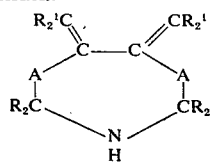

where
   a. each group R may be the same or different group and is selected from the group consisting essentially of
      i. unsubstituted hydrocarbon groups and
      ii. substituted hydrocarbon groups containing a hetero-atom selected from the group consisting of oxygen, sulphur, nitrogen and phosphorus atoms
   and wherein two of said R groups attached to the same ring carbon atom may or may not be linked together to form a second ring
   b. each group R' may be the same or different group and is selected from the group consisting essentially of
      i. hydrogen
      ii. unsubstituted hydrocarbon groups and
      iii. substituted hydrocarbon groups containing a hetero-atom selected from the group consisting essentially of oxygen, sulphur, nitrogen and phosphorus atoms and wherein two of said R' groups attached to the same ring carbon atom may or may be linked together to form a second ring and
   c. each A may be the same or different entity and is selected from the class comprising
      i. a direct link
      ii. the group $-(CH_2)_n-$ where $n$ is an integer
      iii. the group —O—.

2. The stabilized polyolefin as claimed in claim 1 wherein
   a. R is an unsubstituted or substituted hydrocarbon group selected from the group consisting essentially of unsubstituted or substituted alkyl, alicyclic, aryl, aralkyl and alkaryl groups and
   b. R' is hydrogen or an unsubstituted or substituted hydrocarbon group selected from the group consisting essentially of unsubstituted or substituted alkyl, alicyclic, aryl, aralkyl and alkaryl groups.

3. The stabilized polyolefin of claim 1, wherein R is a straight or branched chain alkyl, having 1 to 10 carbon atoms and when said two R groups form a second ring, said two R groups together are of the structure $-(CH_2)-_n$, where $n$ is an integer between 3 and 9.

4. The stabilized polyolefin of claim 2, wherein R is a straight or branched chain alkyl of 1 to 10 carbon atoms.

5. A stabilized polyolefin material according to claim 1 wherein the amine is one in which A represents a direct link.

6. A stabilized polyolefin material according to claim 1 wherein the amine is one in which R$^1$ is hydrogen.

7. A stabilized polyolefin material according to claim 1 wherein the amine is one in which R is a straight chain or branched alkyl group of up to 10 carbon atoms, or the two R groups on the same ring carbon atom are linked to form a spiro-fused 4–10 membered aliphatic ring.

8. A stabilized polyolefin material according to claim 1 wherein the amine is 3,4-dimethylene-2,2,5,5-tetramethylpyrrolidine.

9. A stabilized polyolefin material according to claim 1 wherein the amount of stabilizer is in the range of 0.01 to 1 % by weight of the polyolefin material.

10. A stabilized polyolefin material according to claim 1 wherein the polyolefin is polypropylene.

* * * * *